United States Patent [19]

Kizawa et al.

[11] Patent Number: 4,517,173
[45] Date of Patent: May 14, 1985

[54] MUCOUS MEMBRANE-ADHERING FILM PREPARATION AND PROCESS FOR ITS PREPARATION

[75] Inventors: Hidenori Kizawa; Norimasa Fujiyama, both of Tokyo; Jitsuo Kobayashi, Kanagawa; Akinori Ito, Niigata, all of Japan

[73] Assignee: Nippon Soda Co. Ltd., Tokyo, Japan

[21] Appl. No.: 385,647

[22] PCT Filed: Sep. 25, 1981

[86] PCT No.: PCT/JP81/00254
§ 371 Date: May 25, 1982
§ 102(e) Date: May 25, 1982

[87] PCT Pub. No.: WO82/01129
PCT Pub. Date: Apr. 15, 1982

[30] Foreign Application Priority Data

Sep. 26, 1980 [JP] Japan .................................. 55/33947

[51] Int. Cl.³ ..................... A61L 15/03; A61F 13/00; A61K 9/70
[52] U.S. Cl. ......................................... 424/16; 424/28
[58] Field of Search ..................................... 424/16, 28

[56] References Cited

U.S. PATENT DOCUMENTS 4,136,162 1/1979 Fuchs et al. ........................... 424/28
4,210,633 7/1980 Takruri .................................. 424/28
4,292,299 9/1981 Suzuki et al. .......................... 424/16

FOREIGN PATENT DOCUMENTS

| 822075 | 9/1969 | Canada | 424/28 |
| 0040862 | 12/1981 | European Pat. Off. | 424/28 |
| 45-37038 | 11/1970 | Japan | 424/28 |
| 52-18813 | 2/1977 | Japan | 414/28 |
| 55-62014 | 5/1980 | Japan | 424/28 |
| 56-100714 | 8/1981 | Japan | 424/28 |
| 56-140927 | 11/1981 | Japan | 424/28 |
| 58-59910 | 4/1983 | Japan | 424/28 |

Primary Examiner—Shep K. Rose
Attorney, Agent, or Firm—George B. Oujevolk

[57] ABSTRACT

A mucous membrane-adhering film preparation wherein the film consists of two layers. One layer of the film consists of the pharmaceutical agents and water-soluble high polymer material. The other layer of the film material consists of poor water-soluble agents. The pharmaceutical agent and water-soluble high polymer material layer first layer and the poor water-soluble agents second layer are separately prepared in solvents. The first solution is coated on a base plate having a favorable releasing nature, and, by removing the solvent, the film is produced on the base plate, the second solvent is then coated on the first layer and by removing the solvent, the desired film having one poor water-soluble surface is produced.

2 Claims, 1 Drawing Figure

MUCOUS MEMBRANE-ADHERING FILM PREPARATION AND PROCESS FOR ITS PREPARATION

BACKGROUND OF THE INVENTION

The present invention relates to a preparation which is applied to a mucous membrane and more particularly it relates to a mucous membrane-adhering film preparation which is placed on and adheres onto a mucous membrane part or an inflammed body portion of a mucous membrane to obtain general or local curing effects, and to a process for its preparation.

BRIEF DESCRIPTION OF THE PRIOR ART

Preparations used for applying onto a mucous membrane have become particularly attractive in recent years and give the expectation of quick curing effects by reason of a high concentration of a pharmaceutical agent being absorbed by the mucous membrane and carried directly to the whole body by the body circulatory system, and, these preparations have a lesser loss of the pharmaceutically effective component where the loss occurs by decomposition and chemical or microorganism reactions of the pharmaceutically effective component with the pH condition, digestive juices and microorganisms in the gastric and intestinal organs, such as generally used oral drugs of which the pharmaceutical effective component is absorbed by a gastric wall and the intestinal organs and carried to the whole body after passing through the portal veins and heptic organ.

Troches, buccal tablets, and tongue tablets as preparations for being applied to a mucous membrane in the oral cavity, a suppository, vaginal suppository for use in the rectum and vagina, and an ointment and an adhering tablet as an external preparation applied directly to the inflammed portion are well known as preparations to be applied to the mucous membrane.

However, taking preparations for external use as an example, it is difficult to coat the desired body part alone with the ointment, particularly in the buccal cavity, the staying time of the pharmaceutical component on an ulcerated body part is short because of saliva and the movement of the tongue and cheeks, and the pharmaceutical effect is small in comparison with the amount of dosage and this is a serious drawback. Further, the adhering tablet applied to a larger ulcer stimulates and increases contact pain and furthermore in the event of applying the tablet to several ulcerated parts, several pieces of adhering tablets must be placed on these ulcerated parts and thereby a high pressure of extraneous material is felt on the body parts.

As preparations to overcome these drawbacks, a preparation of the type to adhere to the mucous membrane in the oral cavity or nasal cavity was proposed at the 99th annual meeting of the Japan Pharmaceutical Society (Aug. 28, 1979) and disclosed in the Public Bulletin of Japan Open Patent Publication No. 100714/1981 in which the base agent of the ointment is eccentrically placed in a mucous membrane-adhering coating layer such as cellulose ether.

This preparation has an improved soft flexibility as compared with the conventional adhering tablet, but the size of the preparation is limited.

The present inventors carried out research as to preparations to be applied to the mucous membrane and as a result they have discovered a film preparation which comprises at least two layers: (a) a water-soluble layer containing a pharmaceutical agent, and (b) a poor water-soluble layer; and, wherein the water-soluble layer is to be adhered onto the mucous membrane, and thus, the present invention came into being.

OBJECTS OF THE INVENTION

Therefore, an object of the present invention is to provide a mucous membrane-adhering film preparation which is improved over the defects of the prior art.

Another object of the invention is to provide a process for producing this film preparation.

SUMMARY OF THE INVENTION

Generally speaking, the present invention contemplates a mucous membrane-adhering film preparation which is to be adhered at the side of a pharmaceutical layer onto a mucous membrane, which consists of two layers: (a) a pharmaceutical layer, and (b) a poor water-soluble layer. The pharmaceutical layer (a) consists mainly of pharmaceutical agents and water-soluble high polymers as a film base. The poor water-soluble layer (b) consists mainly of water-soluble high polymers and agents which have poor water-soluble characteristics.

The pharmaceutical agent used herein comprises medical agents or animal agents which can be applied to a mucous membrane or to an inflamed part on a mucous membrane and cures therapeutically or prevents a disease in a whole body or in a local portion. Further it can be used with a pharmaceutical agent which can be dissolved or dispersed in water or organic solvents at room temperature, and, the pharmaceutical agent is preferably chosen from those agents which are discharged gradually whereby a lengthy therapeutical effect can be expected.

Useful pharmaceutical agents contemplated herein include predonisone, predonisolone, predonisolone acetate, hydrocortisone, triamcinolone, dexamethasone, and betamethasone as anti-inflammatory steroids; aspirin, aminopyrin, acetoaminophen, ibufenac, ibuprofen, indomethasine, colehicine, sulpyrine, mephenamic acid, phenacetin, phenylbutazone, fulfenamic acid and probenecid as anti-inflammatory anodynes and ($\alpha$)-chymotrysin as anti-inflammatory enzymes. Further, it comprises anti-histamine agents such as diphenhydramine-hydrochloride, and chlorophenylamine maleate, oral sterilizing agents such as chlorohexydine- hydrochloride, cetylpyridinium-chloride, hexylresorcin and nitrofurazone, antibiotic material such as penicillin or its derivative, cephaphalosporin derivative, erythromycine, tetracycline hydrochloride, furadiomycin, and leucomycin, chemically therapeutic agents such as sulfamethyzole and nalidixic, cardiac strengthening agents such as digatalis and digoxin, blood vein dilating agents such as nitroglycerine and papaverine-hydrochloride, local narcotic agents such as lidocain and procaine-hydrochloride, cough curing agents such as codeine phosphate and bisorlvon, digesting organ curing agents such as azulene, phenovalin, pepsin and vitamin U, enzymes such as lysozyme-chloride or trypsin and anti-diabetic agents such as insulin. Furthermore, it comprises other kinds of agents such as depressing blood pressure agents, tranquilizers, styptic agents, sexual hormones and agents for curing virulent carcinoma or ulcers.

The water-soluble high polymer in the present invention is used for a film base material producing the film preparation and it comprises a natural or synthetic water-soluble high polymer having a superior film moldability and does not give a pharmaceutically undesired influence to the human body or animal body, but is able to produce a soft flexible film.

For example, it can be a water-soluble cellulose derivative such as hydroxypropyl cellulose (hereinafter abbreviated as "HPC"), methyl cellulose, hydroxypropyl alkylcellulose, carboxymethyl cellulose or its salt. Further it comprises an acrylic acid copolymer or its sodium, potassium or ammonium, salt which is obtained by a copolymerization with poly-acrylic acid or its sodium, potassium salt or ammonium salt as a main component and methacrylic acid, styrene or vinyl type of ether (i.e., methyl vinylether or the like) as a comonomer, poly vinyl alcohol, poly vinyl pyrrolidone, polyalkylene glycol, hydroxy propyl starch, alginic acid or its salt, poly-saccharides or those derivatives such as tragacanth, gum gelatine, collagen or denatured gelatin and collagen treated with succinic acid or anhydrous phthalic acid.

As the water-soluble high polymer, one or two or more of the foregoing high polymers may be used, but cellulose derivatives having superior film moldability and producing the soft flexible film are preferably used, and also, "HPC" of the numerous cellulose derivatives, which discharges gradually the effective component is most desired.

In the invention, the mucous membrane-adhering film preparation comprises a high polymer film feeding the poor water-soluble layer onto the single surface of the water-soluble high polymer film, wherein the single surface of the water-soluble high polymer film can be poor water-solubilized by using a process of coating a poor water-soluble layer which is prepared bu adding agents which are poor in water solubility as the poor water-soluble components to a water-soluble high polymer onto the single surface of the water-soluble high polymer film or, a process of partially crosslinking the single surface of the water-soluble high polymer film with an irradiation step or radiation ray or an infrared ray. The process hereinbefore mentioned can be easily carried out and will not cause the denaturing of the pharmaceutical agent, so that it is preferably used.

As agents to be used as the poor water-soluble component which is used by feeding the poor water soluble component to the water-soluble high polymer film, there are: Shellac, higher fatty acids including stearic acid and palmitic acid or the like, and poorly water-soluble cellulose derivatives including ethyl cellulose, cellulose acetate and butyl cellulose can be used by applying these components to the single surface of the water-soluble high polymer film.

The mucous membrane-adhering film preparation of the invention is a pharmaceutical film preparation in which the single surface of the water-soluble high polymer film containing the pharmaceutical agent is treated with the poor water-soluble layer by the process herein described.

The film preparation is a pharmaceutical preparation for application to the mucous membrane in which the film preparation is cut to a desirable size in accordance with the affected diseased body part and a dosage amount of pharmaceutical component, and, it is used by plaster adhesive on the mucous membrane in an oral cavity, nasal cavity, rectum and vagina and thereby a general and/or local therapeutic effect is obtained.

If desired, a plasticizer, a bulking agent, a taste modifying agent, an odor modifying agent and a pigment may be added as additives to the film preparation contemplated herein.

The plasticizer employed for the purpose of appropriately feeding soft flexibility to the film preparation can be polyethylene glycol (macrogol), propyleneglycol, glycerine, copolymer with ethylene oxide and propylene oxide, spun type of fatty acid-lauric ether or an adduct compound which is obtained by adding ethylene oxide or propylene oxide to a compound containing an active hydrogen atom such as sugar cane, sorbitol, glycerine or pentaerythritol. The polyethylene glycol (macrogol) is preferably used when employing "HPC" as the water-soluble high polymer.

As the bulking agent, an agent added to conventional tablets is used such as avicel, mannitol, lactic sugar, sorbitol dextrin, starch, anhydrous calciumphosphate or amylose.

As a taste modifying agent, organic acid compounds for sour taste such as citric acid, tartaric acid, fumaric acid or the like, and sweetening agents such as saccharin, glycyrrhizin or the like and menthol are used.

As an odor modifying agent, a natural or synthetic perfume agent is used. As a pigment, an edible pigment added to conventional tablets is used.

The mucous membrane-adhering film preparation is produced by the following process:

A clear or suspending solution containing one or two kinds or more of said pharmaceutical agent and one or more of said water-soluble high polymer is blended with one or two or more kinds of additives and thereby the first solution (A) is prepared.

A clear or suspending solution containing one or two or more kinds of the agents to be the poor water-soluble component and one, two or more of the water-soluble high polymer is, if desired, blended with one kind or more of said additives and solution (B) is prepared.

The solvents for these solutions (A) and (B) selected, depend on the kind of water-soluble high polymer, pharmaceutical agents, which are to be the poor water-soluble component, and the additives and these concentrations. Water, methanol, ethanol, isopropanol, acetone, methylene chloride and cellusolve or the like may be used or two kinds of these solvents may be used, taking into consideration the volatility of the solvent used. If a control for the residual solvent in the pharmaceutical preparation is taken into consideration, water and/or ethanol are desirably used.

In the event of preparing said solution (B) by using for example, the "MPC" as the water-soluble high polymer, an amount of the agent to be the poor water-soluble component is chosen by weight ratio of MPC/shellack, in the range of 9/1 to 1/9 and the weight ratio of MPC/higher fatty acid in a range of 9/1 to 7/3, and the weight ratio may be optionally chosen by considering a desirable degree of the water-solubility factor.

The solution (A) and the solution (B) as hereinbefore described is coated on a base plate having a favorable releasing nature, for example, a teflon plate or a glass plate, and then, by removing the solvent, a first film is produced, then another material out of solutions (A) and (B) is coated on the single surface of the first film and the solvent is removed, and thereby, the film preparation having a poor water-soluble surface can be produced. The coating procedure of the solution (A) or the solution (B) on the base plate or the prior coated film can be carried out by a brush coating step or an atomizing spray step. But, by setting a frame mold on the base plate and pouring the solution into the frame mold, the thickness of the film can be easily adjusted in a simple and desirable operation.

Removal of the solvent after the coating step is carried out by heating the coated membrane under atmospheric pressure or a reduced pressure.

The film preparation having an optional thickness can be produced by the foregoing process and the film preparation having a total thickness of 1 mm or less does not give an extraneous material sensation when it is placed or made to adhere to the effected mucous membrane. The poor water-soluble layer in the film preparation usually has a thickness of 0.01 to 0.9 mm. Also, a layer which is neither the pharmaceutical agent nor the poor water-soluble agent may be intermediately inserted between the layer containing the pharmaceutical agent and the poor-water-soluble layer. Hereinafter, these are called the "intermediate layer", the "pharmaceutical agent layer", and the "poor water-soluble layer".

The invention as well as other objects and advantages thereof will be better understood from the following detailed description and the accompanying drawing, in which:

FIG. 1 shows an elution test result of the pharmaceutical agent from the film preparation which is obtained in the examples hereinafter described. In the diagram, the ordinate denotes the elution ratio of the pharmaceutical agent in percentage (%) and the abscissa denotes elapsed time in minutes. In FIG. 1, "I" marks show distribution ranges of the elution ratio, and, square marks show average value of the elution ratio of all samples.

DETAILED DESCRIPTION

Example [1]

Figure 1:
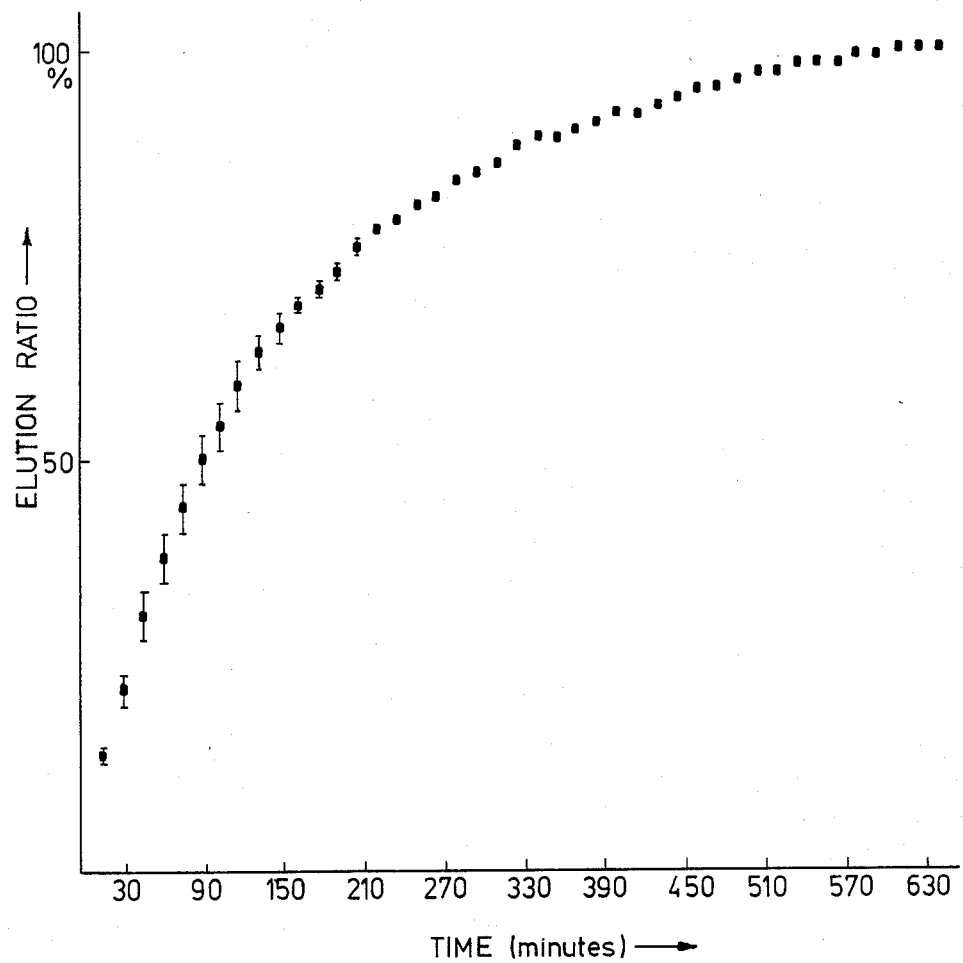

(i) Preparation of the film base agent (a) The solution (A) of the film base agent for preparing the pharmeutical layer:

3.5 g of hydropropyl cellulose and 0.5 ml of macrogol-400 (polyethylene glycol) were dissolved in 63 g of ethyl alcohol and 10 ml of distilled water containing 100 mg of dissolved predonisolone was added to the resulting solution.

(b) The solution (B) for preparing the poor water-soluble layer:

0.5 g of hydroxypropyl cellulose, 0.25 ml of magrogol (polyethylene glycol) and 0.25 g of shellac were dissolved in 6 g of ethyl alcohol.

(c) The solution (C) of the film base agent for preparing the intermediate layer:

3.5 g of hydroxypropyl cellulose and 0.5 ml of magrogol-400 (polyethylene glycol) were dissolved in 63 g of ethyl alcohol.

(ii) The film molding process

The film base agent solution (A) for producing the pharmaceutical agent layer (a) was first poured into the film molding frame (i.e. teflon plate) having 10 cm² of surface area, being placed in a horizontal position. After a drying step, the film base agent solution (C) for preparing the intermediate layer (c) was poured on the film containing the pharmaceutical agent and then, after it had dried, the film base agent solution (B) for preparing the poor water-soluble layer (b) was injected onto it. After a semi-drying step, the laminated film was stripped from the film molding frame. The stripped film was cured at 50° C. temperature for half a day. The film produced consisted of three layers and had a transparency and a soft flexibility.

Further, by almost the same operation, three laminated layer films having different combinations of compositions were obtained as set forth in Table 1.

Example [2]

Instead of the predonisolone in the film base agent of the pharmaceutical layer (a) shown in Example [1], allantoin, i.e. 3-ureido hydantoin) was employed. The two laminated films having different combinations of the composition were obtained from the film base agent solution (A) containing the allantoin and the film base agent solution (B) producing the poor water-soluble layer (b) is set forth in Table 2.

Experimental Example [1]

By using the film preparation in Example [1], an elution test for the pharmaceutical component "predonisolone" was carried out. The test result is set forth in FIG. 1.

The Elution Test Apparatus

Product "VSP (NF)" of Toyama Industry Co., Ltd. Standard Grade: NTR-5S. Aq. Dest. 1,000 ml 37° C. and a basket having 100 rpm rotational velocity.

The Automatic Sampling Apparatus

Product "TAS-30 TC II" of Toyama Industry Co., Ltd. Sampling amount: 10 ml and interval: 15 minutes.

Experimental Example [2]

The film preparation obtained in Example [1] was applied to a patient suffering from "After" type of an oral inflammatory disease. The film preparation is cut to a size slightly larger than the affected area so that the cut piece may contain from 2 to 16 mg of predonisolone and the cut piece was made to adhere onto the affected oral part.

As a result, the film preparation showed favorable adhesive characteristics and it was not stripped off in the course of its therapeutical disposal. In all the examples of applying the invention, a rapid curing effect was recognized.

Further, in using the film preparation of the present invention, the affected part is protected with a soft film and a physical stimulus by the teeth or by food can be avoided. Consequently, the pain which is caused by stress in this disease is greatly mitigated. As a comparison in this respect, a predonisolone tablet having 1.2 mm thickness was made to adhere over the affected part and this time there was a residual pain.

TABLE 1

| Example No. | | | | | | | | |
| --- | --- | --- | --- | --- | --- | --- | --- | --- |
| [1]-1 | | | [1]-2 | | | [1]-3 | | |
| Pharmaceutical agent layer | Intermediate layer | Poor or Difficult water-soluble layer | Pharmaceutical agent layer | Intermediate layer | Poor or Difficult water-soluble layer | Pharmaceutical agent layer | Intermediate layer | Poor or Difficult water-soluble layer |

TABLE 1-continued

| | | | | | | | | | |
|---|---|---|---|---|---|---|---|---|---|
| Predonisolone | 100 mg | — | — | 100 mg | — | — | 100 mg | — | — |
| Hydroxypropyl cellulose | 3.5 g | 3.5 g | 0.5 g | 3.5 g | 2.5 g | 0.5 g | 3.5 g | 2.5 g | 0.5 g |
| Hydroxypropyl methylcellulose | — | — | — | — | — | — | — | — | — |
| Methyl cellulose | — | — | — | — | — | — | — | — | — |
| Macrogol 400 | 0.5 ml | 0.5 ml | 0.25 ml | 0.5 ml | 0.5 ml | 0.25 ml | 0.5 ml | 0.5 ml | 0.25 ml |
| Shellac | — | — | 0.25 g | — | — | 0.25 g | — | — | 0.5 g |
| The used solvent Ethyl alcohol: | | 10:0 | | | 10:0 | | | 10:0 | |

| | | [1]-4 | | | [1]-5 | | |
|---|---|---|---|---|---|---|---|
| | | Pharmaceutical agent layer | Intermediate layer | Poor or Difficult water-soluble layer | Pharmaceutical agent layer | Intermediate layer | Poor or Difficult water-soluble layer |
| | Predonisolone | 100 mg | — | — | 100 mg | — | — |
| | Hydroxypropyl cellulose | 2.0 g | 3.5 g | 0.3 g | 2.0 g | 3.5 g | 0.3 g |
| | Hydroxypropyl methylcellulose | 1.5 g | — | 0.2 g | — | — | 0.2 g |
| | Methyl cellulose | — | — | — | 1.5 g | — | — |
| | Macrogol 400 | 0.6 ml | 0.5 ml | 0.3 ml | 0.6 ml | 0.5 ml | 0.3 ml |
| | Shellac | — | — | 0.25 g | — | — | 0.25 g |
| | The used solvent Ethyl alcohol: | | 8.0:2.0 | | | 7.0:3.0 | |

TABLE 2

| | [2]-1 | | [2]-2 | | [2]-3 | |
|---|---|---|---|---|---|---|
| | Pharmaceutical agent layer | Poor or Difficult water-soluble layer | Pharmaceutical agent layer | Poor or Difficult water-soluble layer | Pharmaceutical agent layer | Poor or Difficult water-soluble layer |
| Allantion | 2.0 g | | 2.0 g | | 2.0 g | |
| Hydroxypropyl cellulose | 3.5 g | 0.75 g | 3.5 g | 0.5 g | 3.5 g | 0.25 g |
| Macrogol 400 | 1.0 ml | 0.25 ml | 1.0 ml | 0.25 ml | 1.0 ml | 0.25 ml |
| Shellac | — | 0.25 g | — | 0.5 g | — | 0.75 g |
| The used solvent | Ethyl alcohol | | Ethyl alcohol | | Ethyl alcohol | |

INDUSTRIAL UTILIZATION

The mucous membrane-adhering film preparation of the present invention is a complex film preparation which consists of a pharmaceutical layer and poor water-soluble layer, or, a pharmaceutical layer, an intermediate layer and a poor water-soluble layer. Consequently, the pharmaceutical layer strongly adheres to the diseased part by absorbing moisture content and then, the pharmaceutical layer becomes wet and swollen. Subsequently, the pharmaceutical agent is gradually dissolved in the diseased part in the course of long hours and the pharmaceutical agent can then be almost homogeneously eluted.

On the other hand, the poor water-soluble layer has poor water solubility and consequently, the pharmaceutical component of the pharmaceutical layer is not eluted and it can be retained in a buccal cavity or the like for long hours without giving a feeling of contacting an extraneous material.

As heretofore mentioned, the film preparation indicates a superior effect which is entirely different from that found in a conventional pharmaceutical preparation.

The following are features of the film preparation of the present invention:

(1) The film preparation can be used for therapeutical purposes on a local diseased part or for the whole body.

(2) Because of the gradual discharge of the pharmaceutical component, the useful hours are long and less stimulation is given to the diseased part.

(3) The film preparation can be used for the musous membrane or the diseased part wetted with a diffused liquid or a secreted liquid.

(4) The film preparation can be cut to any size and thereby a predetermined amount of the pharmaceutical agent may be used.

(5) The film preparation protects the diseased part from physical harm.

(6) many different pharmaceutical agents can be used for the film preparation.

(7) The film preparation may be provided with an adhesive.

(8) The film preparation has a soft flexibility.

(9) Even if the film base agent is swallowed, it is not absorbed in the walls of the internal organs.

(10) The film preparation has low toxicity and is safe.

It is to be observed therefore that the present invention provides a novel film preparation for applying to the mucous membrane and to the process of producing the preparation.

What is claimed is:

1. A mucous membrane-adhering film preparation with a flat contact side so formed as to be applied to an oral cavity and to adhere onto a mucous membrane, said preparation consisting of at least three layers, namely, a pharmaceutical layer (a), a poor water-soluble layer (b), and an intermediate layer (c), wherein:

(a) said pharmaceutical layer (a) is a material selected from the group consisting of predonisolone and allantoin together with water-solluble cellulose derivatives selected from the group consisting of hydroxypropyl cellulose, methyl cellulose, hydroxy propyl methyl cellulose and mixtures thereof, as a thin film base;

(b) said poor water-soluble layer (b) consists of water-soluble cellulose derivative together with poor-water-soluble components, said components being selected from the group consisting of shellack, higher fatty acids, and mixtures thereof; and, (c) said intermediate layer consists of water-soluble cellulose derivatives not containing a pharmaceutical agent and not-containing poor water-soluble components.

2. A preparation as claimed in claim 1 wherein the water-soluble cellulose derivatives are selected so as to have superior film moldability so as to produce a soft flexible film and the hydroxypropyl cellulose, methyl cellulose, hydroxy propyl methyl cellulose and mixtures thereof are so selected as to gradually discharge the effective components in the mouth.

* * * * *